United States Patent
Mineau-Hanschke

(10) Patent No.: US 6,582,391 B2
(45) Date of Patent: Jun. 24, 2003

(54) HYBRID MATRIX IMPLANTS AND EXPLANTS

(75) Inventor: Rochelle Mineau-Hanschke, Waltham, MA (US)

(73) Assignee: Transkaryotic Therapies, Inc., Cambridge, MA (US)

(*) Notice: Subject to any disclaimer, the term of this patent is extended or adjusted under 35 U.S.C. 154(b) by 0 days.

(21) Appl. No.: 10/188,628

(22) Filed: Jul. 2, 2002

(65) Prior Publication Data

US 2003/0077260 A1 Apr. 24, 2003

Related U.S. Application Data

(62) Division of application No. 09/312,246, filed on May 14, 1999, now Pat. No. 6,472,181, which is a division of application No. 08/548,002, filed on Oct. 25, 1995, now Pat. No. 5,965,125.

(51) Int. Cl.$^7$ .......................... A61N 1/30; A61M 37/00; A61K 9/22; A61K 48/00; C12N 5/00
(52) U.S. Cl. .......................... 604/19; 604/4; 604/890.1; 424/93.1; 424/93.21; 435/325; 435/382; 435/289.1; 435/297.1
(58) Field of Search .......................... 604/4, 890.1, 19, 604/481, 51, 52, 53, 85; 424/93.21, 93.1; 435/325, 382, 174, 289.1, 297.1, 297.2, 297.4

(56) References Cited

U.S. PATENT DOCUMENTS

| | | |
|---|---|---|
| 4,485,096 A | 11/1984 | Belt |
| 4,604,346 A | 8/1986 | Bell et al. |
| 4,686,098 A | 8/1987 | Kopchick et al. |
| 4,837,379 A | 6/1989 | Weinberg |
| 4,861,714 A | 8/1989 | Dean, Jr. et al. |
| 4,863,856 A | 9/1989 | Dean, Jr. et al. |
| 4,963,489 A | 10/1990 | Naughton et al. |
| 4,997,753 A | 3/1991 | Dean, Jr. et al. |
| 5,032,550 A | 7/1991 | Derkacy |
| 5,100,783 A | 3/1992 | Dean, Jr. et al. |
| 5,266,480 A | 11/1993 | Naughton et al. |
| 5,270,192 A | 12/1993 | Li et al. |

FOREIGN PATENT DOCUMENTS

| | | |
|---|---|---|
| EP | 0338716 A2 | 11/1989 |
| EP | 0 344 924 A2 | 12/1989 |
| EP | 0 361 957 A1 | 4/1990 |
| EP | 0 418 035 A1 | 3/1991 |
| EP | 0 419 111 A1 | 3/1991 |
| EP | 0 457 430 A2 | 11/1991 |
| FR | 2 704 236 | 10/1994 |
| FR | 2 708 202 | 2/1995 |
| WO | 80/01350 | 7/1980 |
| WO | WO 93/09222 | 5/1993 |
| WO | 94/10950 A1 | 5/1994 |
| WO | WO 94/12650 | 6/1994 |
| WO | WO 94/24298 | 10/1994 |
| WO | WO 95/19430 | 7/1995 |
| WO | WO 95/26761 | 10/1995 |

OTHER PUBLICATIONS

Remmler et al., "Use of Injectable Cultured Human Fibroblasts . . . ", Jul. 1989, Arch Otolaryngol Head Neck Surg, vol. 115;837–844.

Bartlett et al., "Regulation of neural stem cell differentiation in the forebrain," Immunol. Cell. Biol. 76(5):414–418, 1998 (Abstract only).

Bell et al., Production of a Tissue–like Structure by Contraction of Collagen Lattices by Human Fibroblasts of Different Proliferative Potential In Vitro, Proc. Natl. Acad. Sci. USA 76:1274–1278, 1979.

Bell et al., Recipes for Reconstituting Skin, J. Siomechanical Engineering 113:113–119, 1991.

Bergsteindottir et al., The Effect of Three Dimensional Collagen Type I Preparation on the Structural Organization of Guinea Pig Enteric Ganglia in Culture, Experimental Cell Research 209:64–75, 1983.

Bisbee et al., Mouse Mammary Epithelial Cells on Floating Collagen Gels: Transepithelial Ion Transport Effects of Prolactin, Proc. Natl. Acad. Sci. USA 76:536–540, 1979.

Boyce et al., Biologic Attachment, Growth, and Differentiation of Cultured Human Epidermal Keratinocytes on a Graftable Collagen and Chondroitin–6–Sulfate Substrate, Surgery 103:421–430,1988.

Chen et al., "Differential roles for bone morphogenetic protein (BMP) receptor type IB and IA in differentiation and specification of mesenchymal . . . lineages," J. Cell. Biol. 142(1):295–305, 1998 (Abstract only).

Demetriou et aL.,,Replacement of Liver Function in Rats by Transplantation of Microcarrier–Attached Hepatocytes, Science 233:1190–1192, 1986.

Elsdale and Bard, Collagen Substrata for studies on Cell Behavior, J. Cell Biology 54:626–627, 1972.

Emerman and Pitelka, Maintenance and Induction of Morphological Differentiation in Dissociated Mammary Epithelium on Floating collagen Membranes, In Vitro 13:316–328, 1977.

(List continued on next page.)

Primary Examiner—David Guzo
Assistant Examiner—Quang Nguyen
(74) Attorney, Agent, or Firm—Fish & Richardson PC

(57) ABSTRACT

An implantable device having a body of matrix material made up of insoluble collagen fibrils, and disposed therewithin (a) a plurality of vertebrate cells; and (b) a plurality of microspheres each of which consists primarily of one or more of the following materials: collagen, polystyrene, dextran, polyacrylamide, cellulose, calcium alginate, latex, polysulfone, or glass.

20 Claims, 3 Drawing Sheets

OTHER PUBLICATIONS

Gilbert et al., Cell Transplantation of Genetically Altered Cells on Biodegradable Polymer Scaffolds Syngeneic Rats, Transplantation 56:423–427, 1993.

Gregoire et al., "Understanding adipocyte differentiation," Physiol. Rev. 78(3):783–809, 1998 (Abstract only).

Halberstadt et al., The In Vitro Growth of a Three–Dimensional Human Dermal Replacement Using a Single⁻Pas.Ω Perfusion System, Biotechnology and Bioengineering 43:740–746, 1994.

Hansbrough et al., "Evaluation of a biodegradable matrix containing cultured human fibroblasts as a dermal eplacement beneath meshed skin grafts on athymic mice," Surgery, 11:438–446, 1992.

Kleinman ofet at., Role of Coltagenous Matrices in the Adhesion and Growth Cells, J. Cell Biology 88:473–485, 1981.

Krueger et al., Genetically Modified Skin to Treat Disease: Potential and Limitations, J. Investigative Dermatology, 103:765–845, 1994.

Moullier et. Al., Long–term Delivery of a Lysosomal Enzyme by Genetically Modified Fibroblasts in Dogs, Nature Medicine 1995.

Moullier et al., Correction of Lysosomal Storage in the Liver and Spleen of MPS VII Mice by Implantation of Genetically Modified Skin Fibroblasts, Nature Genetics 4:154:159, 1993.

Moullier et al., Continuous Systemic Secretion of a Lysosomal Enzyme by Genetically Modified Mouse Skin Fibroblasts, Transplantation 56:427–432, 1993.

Nakajima et al., Adipose tissue extracellular matrix: newly organized by adipocytes during differentiation Differentiation 63(4):193–200, 1998 (Abstract only).

Nakagawa et at., Long–term Culture of Fibroblasts in Contracted Collagen Gels: Effects on Cells Growth and Biosynthetic Activity, J. Investigative Dermatology 93:792–798, 1989.

Palmer et at., Genetically Modified Skin Fibroblasts Persist Long After Transplantation but Gradually Inactivate Introduced Genes, Proc. Natl. Acad. Sci. USA 88:1330–1334, 1991.

Palmer et at., Production of Human Factor IX in Animals by Genetically Modified Skin Fibroblasts: Potential Therapy for Hemophilia B,, Blood 73:438–445, 1989.

Reuveny, Microcarriers in Cell Culture: Structure and Applications, Advances in Cell Culture 4:213–47, 1985.

Shahar et at., Cerebral Neurons, Skeletal Myoblasts, and Cardiac Muscle, Biotechnology and Bioengineering 43:826–831, 1994.

St. Louis et al. An Alternative Approach to Somatic Cell Gene Therapy (1988), Proc. Natl. Sci. USA 85:3150–3154.

Sullivan et al., "Biohybrid Artificial Pancreas: Long–Term Implantation Studies in Diabetic, Pancreatectomized Dogs," Science 252:718–721, May 3, 1991.

Turley et at., The Retention and Uttrastructural Appearances of Various Extracetlular Matrix Molecules Incorporated into Three–Dimensional Hydrated Collagen Lattices, Developmental Biology 109:347–369, 1985.

Varani et at., Cell Growth on Microcarriers: Comparison of Proliferation on and Recovery from Various Substrates J. Biological Standardization 14:331–336, 1986.

Vournakis and Runstadler, Microenvironment: The Key to Improved Cell Culture Products, Bio/Technology 7:143–145, 1989.

Weinberg and Bell, Regulation of Proliferation of Bovine Aortic Endothelial Cells, Smooth Muscle Cells, a Adventitial Fibroblasts in Collagen Lattices, J. Cellular Physiology 122:410–414, 1985.

Freshney, (ed.), Culture of Human Cells, 3rd Edition, Wiley-Liss, Inc., 1994, pp. 219–224.

Wilkens et al., "Development of a bilayered living skin construct for clinical applications," Biotech Bioeng. 43:747–756, 1994.

Product Description for Unweighted Macroporous Microspheres, "Cellex Biosciences Technical Note," Biosciences, Inc., 10 pages, 1994.

Product Description for Verax® microspheres, "Verax VX–100® Microspheres Technical Specifications," Verax Corporation, 2 pages, 1991.

Wivel et al., "Method of Gene Delivery", 1998, Hematology/Oncology Clinics of North America, vol. 12(3):483–501.

Dang et al., "Gene Therapy and Translational Caner Research", 1999, Clinical Research, vol. 5;471–474.

Riddell et al., "T–Cell Mediated Rejection of Gene–Modified . . . ", 1996, Nature Medicine, vol. 2(2);216–223.

Kohn et al., "Gene Therapy for haematopoietic and lymphoid disorders", 1997, Clin. Exp. Immunol, vol. 107;54–57.

HYBRID MATRIX IMPLANTS AND EXPLANTS

RELATED APPLICATIONS

This application is a divisional of U.S. application Ser. No. 09/312,246, filed May 14, 1999, now U.S. Pat. No. 6,472,181, which is a divisional of U.S. application Ser. No. 08/548,002, filed Oct. 25, 1995, now U.S. Pat. No. 5,965,125.

The field of the invention is medical devices used in vivo or in vitro for production and delivery of medically useful substances.

BACKGROUND OF THE INVENTION

The means used to deliver medically useful substances can significantly affect their efficacy. The standard route of administration for many such substances is either oral, intravenous, or subcutaneous. Each has inherent limitations which can affect the therapeutic utility of the substances being delivered. For example, many protein-based drugs have short half-lives and low bioavailabilities, factors that must be considered in their formulation and delivery. Although various devices have been developed to deliver medically useful substances, including portable pumps and catheters, there is still a significant need for improved delivery devices.

Many medically useful substances, including proteins, glycoproteins, and some peptide and nonpeptide hormones, are more efficiently produced by cultured cells than via artificial synthetic routes. Appropriate cells are typically cultured in bioreactors, and the desired product purified therefrom for administration to the patient by standard means, e.g. orally or by intravenous or subcutaneous injection. Alternatively, the cells may be implanted directly into the patient, where they produce and deliver the desired product. While this method has a number of theoretical advantages over injection of the product itself, including the possibility that normal cellular feedback mechanisms may be harnessed to allow the delivery of physiologically appropriate levels of the product, it introduces additional complexities. One of these concerns the appropriate environment for the cells at the time of implantation. It would be desirable to organize the cells of the implant in a form that is compatible with the natural in vivo environment of the cell type comprising the implant (fibroblasts, for example, exist naturally in a rich network of extracellular matrix composed primarily of collagen). There is also a need in some cases to ensure that the implanted cells remain localized to a defined site in the patient's body, so that they can be monitored and perhaps removed when no longer needed.

One technique that has been tested for this purpose utilizes an implantation device consisting of a solid, unitary piece of collagen gel (a "collagen matrix") in which the cells are embedded (e.g., Bell, U.S. Pat. No. 4,485,096). Other substances, such as polytetrafluoroethylene (PTFE) fibers (Moullier et al., Nature Genetics, 4:154, 1993; WO 94/24298), may be included in the collagen implant to impart strength or other desirable characteristics to the collagen gel.

SUMMARY OF THE INVENTION

It has been found that the function of collagen matrices can be substantially improved by the addition of microspheres to the collagen matrix, thereby forming what is herein termed a "hybrid matrix". This may be accomplished by mixing microspheres with the cells and soluble collagen prior to gelling of the collagen to form the matrix. If desired, the microspheres and cells can be cultured together for a period which permits the cells to adhere to the microspheres before addition of the non-gelled collagen solution; alternatively, the three constituents can be mixed essentially simultaneously or in any desired order, followed by gelation of the soluble collagen within the mixture, to form a gelled mixture consisting of insoluble collagen fibrils, cells and microspheres. This gelled mixture gradually becomes smaller through the exclusion of liquid to form a solid, relatively resilient, implantable unit that contains both the microspheres and the cells embedded in the insoluble collagen fibril network. When the microspheres are also composed largely of collagen, the resulting matrix is herein termed a "hybrid collagen matrix".

The invention thus includes an article or device having a body made of matrix material that includes insoluble collagen fibrils, and disposed within the body:

(a) a plurality of vertebrate cells (particularly mammalian cells such as cells derived from a human, chimpanzee, mouse, rat, hamster, guinea pig, rabbit, cow, horse, pig, goat, sheep, dog, or cat); and (b) a plurality of microspheres (or beads), each of which consists primarily of (i.e., greater than 50% of its dry weight is) one or more substances selected from a list including collagen (preferably type I collagen), polystyrene, dextran, polyacrylamide, cellulose, calcium alginate, latex, polysulfone, and glass (e.g., glass coated with a gel such as collagen, to improve adherence of cells). Generally at least 70%, and preferably at least 80% (most preferably between approximately 90% and approximately 100%, e.g., at least 95%) of each microsphere's dry weight is one or more of the listed substances. Commercial examples of microspheres which are described as consisting essentially of purified collagen include ICN Cellagen Beads and Cellex Biosciences macroporous microspheres. The microspheres are preferably of a porous consistency, but may be smooth, and typically have an approximately spherical shape with a diameter of approximately 0.1 to 2 mm (e.g., between approximately 0.3 and 1 mm). Of course, the shape and size of microspheres from any particular lot or preparation will vary within manufacturing tolerances. The article may be configured to be implanted into an animal, e.g., a mammal such as a human patient, or may be designed for producing cellular products in vitro; e.g., in an extracorporeal bioreactor apparatus having a means for shunting blood from an animal to the article and then back into a blood vessel of the animal, or in a bioreactor or other vessel from which medium containing the desired cellular product can be recovered for purification and the preparation of a pharmaceutical agent. The cells may be derived from one or more cells removed from the patient, and preferably are transfected cells containing exogenous DNA encoding one or more medically useful polypeptides such as an enzyme, hormone, cytokine, colony stimulating factor, angiogenesis factor, vaccine antigen, antibody, clotting factor, regulatory protein, transcription factor, receptor, or structural protein. Examples of such polypeptides include human growth hormone (hGH), Factor VIII, Factor IX, erythropoietin (EPO), albumin, hemoglobin, alpha-1 antitrypsin, calcitonin, glucocerebrosidase, low density lipoprotein (LDL) receptor, IL-2 receptor, globins, immunoglobulins, catalytic antibodies, the interleukins, insulin, insulin-like growth factor 1 (IGF-1), parathyroid hormone (PTH), leptin, the interferons, nerve growth factors, basic fibroblast growth factor (bFGF), acidic FGF (aFGF), epidermal growth factor (EGF), endothelial cell growth factor, platelet derived growth factor (PDGF), transforming growth factors, endothelial cell stimulating angiogenesis factor (ESAF), angiogenin, tissue plasminogen activator (t-PA), granulocyte colony stimulating factor (G-CSF), and granulocyte-macrophage colony stimulating factor (GM-CSF). Alternatively, the exogenous DNA can be a regulatory sequence that will activate expression of an endogenous gene (for example, using homologous recombination as described in WO94/12650-PCT/US93/11704, which is incorporated by referenced herein).

Generally any type of cell which is capable of attaching to collagen and/or the microspheres, and which exhibits a desirable property such as expression of a medically useful cellular product or performance of an essential structural or metabolic function, can be utilized in the matrices of the invention. Examples include adipocytes, astrocytes, cardiac muscle cells, chondrocytes, endothelial cells, epithelial cells, fibroblasts, gangliocytes, glandular cells, glial cells, hematopoietic cells, hepatocytes, keratinocytes, myoblasts, neural cells, osteoblasts, pancreatic beta cells, renal cells, smooth muscle cells and striated muscle cells, as well as precursors of any of the above. If desired, more than one type of cell can be included in a given matrix. The cells may be present as clonal or heterogenous populations.

The collagen in the matrix material is preferably type I, but may be any other type of collagen. The matrix material may optionally include two or more types of collagen (e.g., selected from types I, II, III, IV, V, VI, VII, VIII, IX, X, and XI), as well as any additional components that impart desirable characteristics to the resulting matrix: e.g., agarose, alginate, fibronectin, laminin, hyaluronic acid, heparan sulfate, dermatan sulfate, chondroitin sulfate, sulfated proteoglycans, fibrin, elastin, or tenascin. Any of the above mentioned collagenous and non-collagenous components may be derived from human sources or from another animal source. One could also include collagen or non-collagen fibers disposed within the device. Such fibers can, for example, be made of a material that includes nylon, dacron, polytetrafluoroethylene, polyglycolic acid, polylactic/polyglycolic acid polymer mixtures, polystyrene, polyvinylchloride co-polymer, cat gut, cotton, linen, polyester, or silk.

Large numbers of cells can be contained within the hybrid matrices. For example, hybrid matrices can be prepared which contain at least approximately two (and preferably approximately three) times as many cells as matrices prepared with soluble collagen alone, assuming the number of cells inoculated and the initial production volume are equivalent. The total amount of polypeptide expressed by the cells embedded in a given hybrid matrix in a given time period is typically significantly higher (e.g., at least 50% higher, preferably at least 100% higher, and more preferably at least 200% higher) than achieved with a standard collagen matrix of equivalent volume.

The hybrid matrix of the invention is generally prepared by a process that includes the following steps:

forming a mixture that includes (a) a plurality of vertebrate cells; (b) a plurality of microspheres, each of which consists primarily of one or more substances selected from the list consisting of collagen, polystyrene, dextran, polyacrylamide, cellulose, calcium alginate, latex, polysulfone, and glass; and (c) a solution comprising soluble collagen;

causing the soluble collagen in the mixture to form a gel of insoluble collagen fibrils in which the cells and the microspheres are embedded; and exposing the gel to culture conditions which cause the gel to become smaller by the exclusion of liquid, thereby forming the body of the article. Gelation is typically triggered by raising the pH of the relatively acidic collagen solution to above 5, e.g., by addition of concentrated, buffered culture medium, whereupon the collagen forms insoluble fibrils. When this step is carried out in a mold, the gel will take the shape of the interior of the mold. Generally the contraction of the gel is effected by the cells in the mixture, which attach to the fibrils and cause it to contract to a smaller version of the molded shape (e.g., a disk, as in the case where the mold is a petri dish which is cylindrical in shape). The matrix may be utilized immediately after manufacture, may be cultured to increase the number of cells present in the matrix or to improve their functioning, or may be cryopreserved indefinitely at a temperature below 0C.

A medically useful polypeptide, such as one listed above, may be delivered to a patient by a treatment method that involves providing a hybrid matrix containing cells which secrete the polypeptide of interest, and implanting the article in the patient in a selected site, such as a subcutaneous, intraperitoneal, sub-renal capsular, inguinal, intramuscular or intrathecal site. Where the polypeptide is one which promotes wound healing (e.g., PDGF or IGF-I), the matrix may be implanted at the site of a preexisting wound. As discussed above, the cells may be derived from one or more cells removed from the patient, and are preferably transfected in vitro with exogenous DNA encoding the polypeptide. Alternatively, they may be cells which naturally secrete the polypeptide or perform the desired metabolic function (e.g., hepatocytes or pancreatic beta cells).

In another embodiment, the medically useful polypeptide may be administered to the patient by shunting a portion of the patient's blood through the apparatus described above, so that the polypeptide secreted by the cells in the hybrid matrix mixes with the blood. Generally, any such apparatus known to those in that field can be adapted to accommodate the matrix of the invention. For example, blood shunted into a device which contains a perm-selective membrane surrounding a matrix of the present invention will result in the delivery of a therapeutic product of the matrix to the blood. A device similar to an artificial pancreas (Sullivan et al., Science 252:718–721, 1991) may be used for this purpose.

Yet another use for the hybrid matrices of the invention is as a means for producing a polypeptide in vitro. This method includes the steps of placing the hybrid matrix under conditions whereby the cells in the matrix express and secrete the polypeptide; contacting the matrix with a liquid such that the cells secrete the polypeptide into the liquid; and obtaining the polypeptide from the liquid, e.g., by standard purification techniques appropriate for the given polypeptide. In one embodiment, the matrix is anchored to a surface and is bathed by the liquid; alternatively, the matrix floats freely in the liquid. Cells embedded in the hybrid matrix function at a high level in a small space. Furthermore, the first step in purification of the expressed polypeptide (removal of the cells from the medium) is considerably more efficient with the matrices than with most standard methods of cell culture.

Other features and advantages of the invention are apparent from the claims, and from the detailed description provided below.

DETAILED DESCRIPTION

Figure 1:
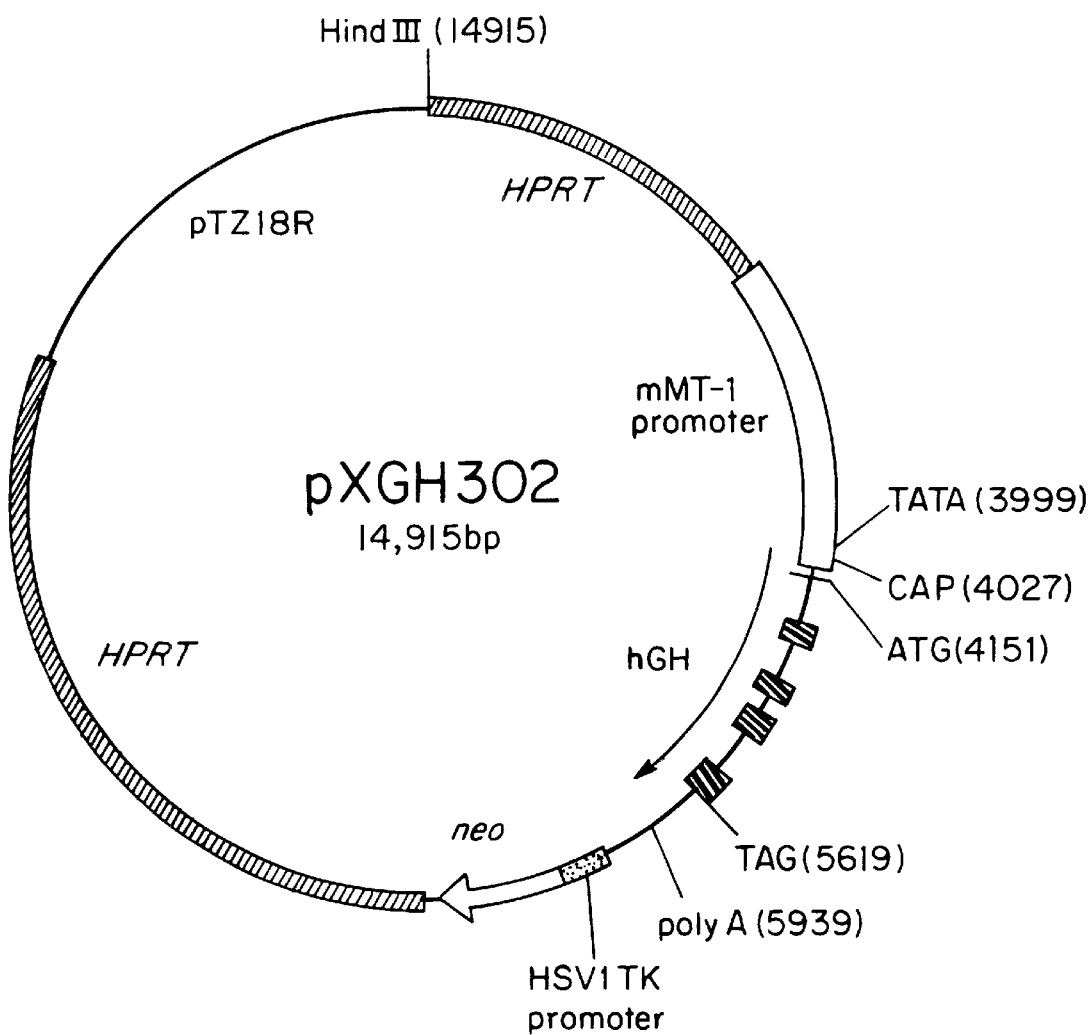
FIG. 1 is a map of hGH expression plasmid pXGH302.

The examples set forth below illustrate several embodiments of the invention. These examples are for illustrative purposes only, and are not meant to be limiting.

Example I

This example describes the procedures utilized to prepare a clonal cell strain of human fibroblasts stably transfected with the plasmid pXGH302 secreting recombinant human growth hormone (hGH), and to combine them with porous collagen microspheres in a hybrid matrix of the invention. Such matrices are referred to as hybrid collagen matrices (HCM).

A. Generation of Primary Human Fibroblasts Expressing Human Growth Hormone

Fibroblasts were isolated from freshly excised human foreskins by an enzymatic dissociation technique. Upon confluency, primary cultures were dislodged from the plastic surface by mild trypsinization, diluted and replated to produce the secondary cell culture for transfection.

Plasmid pXGH302 was constructed as described in Example II, and transfection was carried out by electroporation, a process in which cells are suspended in a solution of plasmid DNA, placed between a pair of oppositely charged electrodes, and subjected to a brief electric pulse.

Treated cells were selected in G418-containing medium for 10–14 days. Cells that integrated the plasmid into their genomes stably expressed the product of the neo gene and formed colonies resistant to killing by the neomycin analog G418. Each colony, consisting of a clonal population of cells, was individually removed from its position on the tissue culture dish by trypsinization. Those clones scoring positive for hGH expression were expanded for quantitative assays, and clone HF165-24 was chosen for further use.

Further detailed procedures for preparing and transfecting cells suitable for use in the matrices of this invention are provided in WO93/09222 (PCT/US92/09627), which is incorporated herein by reference.

B. Preparation of Hybrid Collagen Matrices

1. Microsphere Preparation

Collagen microspheres (Cellex Biosciences cat. #YB00-0015UW) were transferred from each original bottle provided by the manufacturer (~10 ml per bottle) into 50 ml conical tubes (1 tube per bottle). The microspheres were allowed to settle in the tube, and the storage buffer solution was aspirated off. Microsphere wash medium (DMEM with 1% calf serum and 1% penicillin/streptomycin) was added to the 50 ml mark on the graduated tube, the microspheres allowed to settle, and the medium aspirated off. This series of washing steps was repeated for a total of 4 washes. The microspheres were transferred to a 250 ml Erlenmeyer flask using a 25 ml plastic pipette, limiting the volume of microspheres to 100 ml per 250 ml flask. Microsphere wash medium was added to the 250 ml mark, and the flask was capped and placed in a tissue culture incubator at 37° C. for 2–3 hours. The flask was removed from the incubator, the microspheres allowed to settle, and the wash medium aspirated off. This series of incubation and washing steps was repeated for a total of 3 washes.

2. Hybrid Collagen Matrix Preparation

The cells and microspheres were mixed just prior to adding the collagen solution. Washed microspheres were added to 15 ml graduated conical tube(s) to the desired volume (volume=no. of matrices multiplied by 1 ml; see Table 1). Microspheres were allowed to settle for at least 10 minutes before measuring volume. Excess wash medium was removed by aspiration.

Cells to be embedded in the matrix were harvested by trypsinization and the cell number was determined. The required number of cells (cell no. per matrix multiplied by total no. of matrices to be produced) was centrifuged at 1500 rpm (500 xg) for 7 min at room temperature. In an appropriately sized conical-bottom polypropylene tube, a mixture of equal volumes of modified 2x DMEM (2x DMEM with 9 g/L glucose, 4 mM L-glutamine, and 22.5 mM HEPES) and calf serum was prepared according to Table 1. (Note: for volumes greater than 250 ml, the total pooled volume should be divided into appropriately sized tubes.) The cell pellet was resuspended in the 2x DMEM-calf serum mixture. The collagen microspheres were mixed with the cell suspension by adding 1–2 ml of the cell suspension to the packed microspheres and then transferring the concentrated microspheres by 10 ml pipette into the remaining cell suspension, followed by gentle mixing with the pipette. The mixture was placed on ice and the appropriate volume of collagen solution was added (rat tail Type I collagen; UBI cat #08-115, diluted to concentration of 4.0 mg/ml in 0.02 M acetic acid), as indicated in Table 1. The contents of the tube were mixed carefully (avoiding creating bubbles or frothing) using a 10 ml glass pipette, until the matrix solution appeared homogenous.

To produce the matrix, an appropriate volume of the collagen/cell/microsphere/medium mix was added to a sterile petri dish with a pipette (10 or 25 ml capacity), according to the total volume per dish listed in Table 1. (The mix was agitated by pipetting occasionally during the filling of dishes to prevent settling of cells or microspheres.) The filled dishes were placed in a 37° C., 5% $CO_2$, 98% relative humidity tissue culture incubator and left undisturbed for approximately 24 h, during which time the contents gelled and the size of the gel decreased in all dimensions to form the hybrid matrices of the invention, which were approximately 50% of the diameter and 10% of the volume of the non-gelled mixture.

Figure 2:
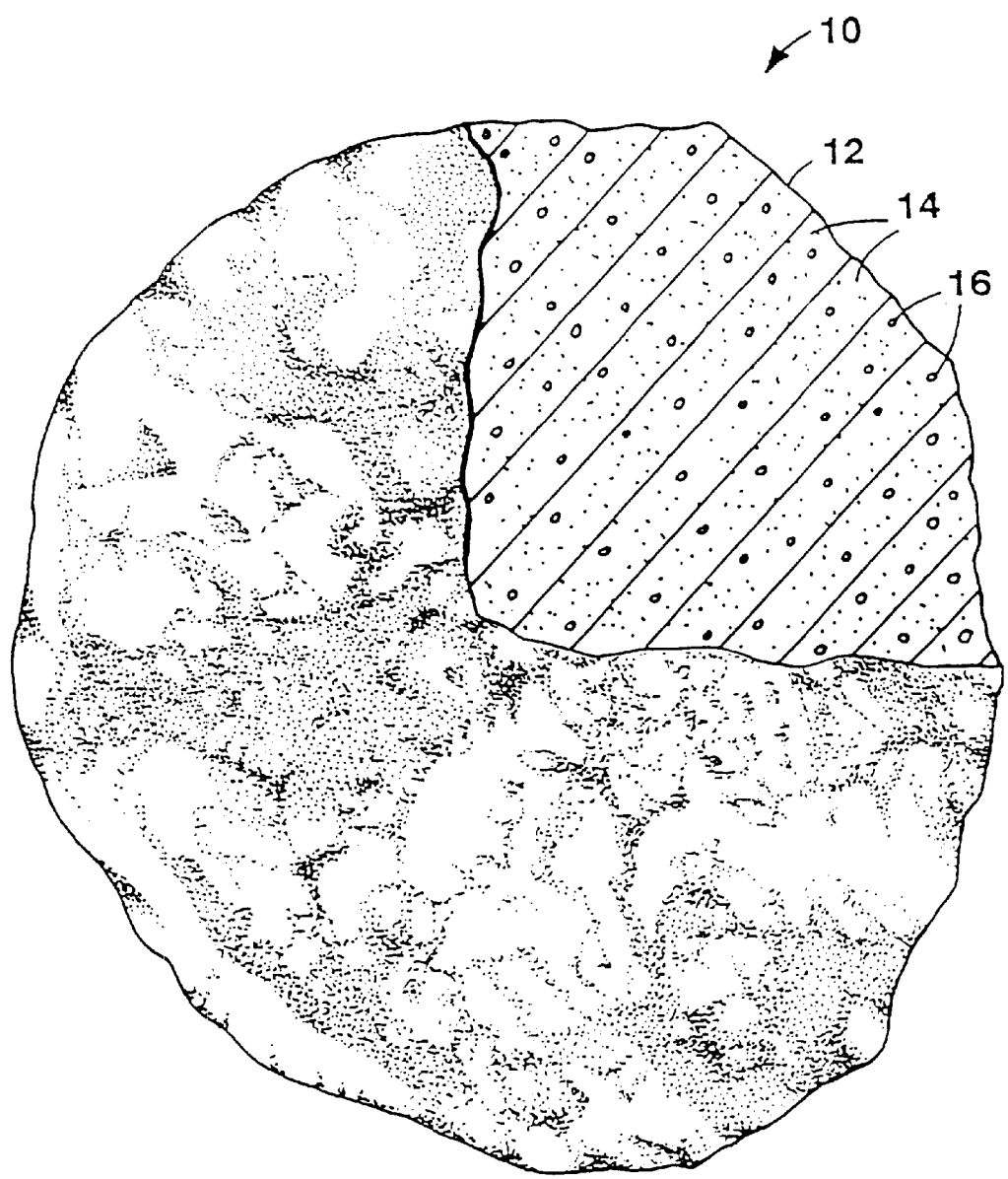
FIG. 2 is a plan view in partial section of one embodiment of the invention.

One embodiment of the hybrid matrix of the invention is illustrated in FIG. 2. The matrix 10 consists of a contracted collagen gel body 12 in which are embedded vertebrate cells 14 and microspheres 16. For clarity in this figure, the cells are shown as dots separate from the microspheres. In fact, most of the cells would be expected to be attached to the microspheres, and would be substantially smaller than represented in the figure.

TABLE 1

Medium, Microsphere, and Collagen Volumes Required for HCM Production

| Dish Size | Number of Matrices | Modified 2x DMEM | Serum | Microspheres | Collagen Solution | Total Vol. |
| --- | --- | --- | --- | --- | --- | --- |
| 60 mm | 1 | 1 ml | 1 ml | 1 ml | 1 ml | 4 ml |
| 60 mm | 12 | 12 ml | 12 ml | 12 ml | 12 ml | 48 ml |
| 100 mm | 1 | 2.5 ml | 2.5 ml | 2.5 ml | 2.5 ml | 10 ml |
| 100 mm | 12 | 30 ml | 30 ml | 30 ml | 30 ml | 120 ml |
| 150 mm | 1 | 7.5 ml | 7.5 ml | 7.5 ml | 7.5 ml | 30 ml |
| 150 mm | 12 | 90 ml | 90 ml | 90 ml | 90 ml | 360 ml |

Example II pXGH302 was constructed by subcloning the 6.9 kb HindIII fragment extending from positions 11,960–18,869 in the human HPRT sequence (Edwards et al., *Genomics*, 6:593–608, 1990; Genbank entry HUMHPRTB) and including exons 2 and 3 of the HPRT gene, into the HindIII site of pTZ18R (Pharmacia P-L Biochemicals, Inc.). The resulting clone was cleaved at the unique XhoI site in exon 3 of the HPRT gene fragment, and the 1.1 kb SalI-XhoI fragment containing the neo gene from pMClNeo (Stratagene) was inserted, disrupting the coding sequence of exon 3. One orientation, with the direction of neo transcription opposite that of HPRT, was chosen and designated pE3neo.

To combine the hGH gene, HPRT sequences, and neo gene in the same plasmid, pXGH5 (Selden et al., Mol. Cell. Biol. 6:3173–3179, 1986) was digested with EcoRI, and the 4.0 kb fragment containing the hGH gene and linked mouse metallothionein-I (mMT-I) promoter was isolated. The ExoRI overhangs were filled in with the Klenow fragment from *E. coli* DNA polymerase. pE3Neo was digested with XhoI, which cuts at the junction of the neo fragment and HPRT exon 3 (the 3' junction of the insertion into exon 3). The XhoI overhanging ends of the linearized plasmid were filled in with the Klenow fragment from *E. coli* DNA polymerase, and the resulting fragment was ligated to the 4.0 kb blunt-ended mMT/hGH fragment. Bacterial colonies derived from the ligation mixture were screened by restriction enzyme analysis for a single copy insertion of the mMT-I/hGH fragment. One subclone, in which the hGH gene is transcribed in the same direction as the neo gene, was designated pXGH302. A map of plasmid pXGH302 is shown in FIG. 1. In this figure, the position and orientation of the hGH coding region and the mouse metallothionein-I promoter (mMT-I) controlling hGH expression are noted. The positions of basal promoter elements (TATA), transcription initiation sites (CAP), and translation initiation sites (ATG) are indicated. As illustrated, neo gene transcription is controlled by the polyoma enhancer/herpes simplex virus (HSV) thymidine kinase (TK) gene promoter. HPRT denotes the positions of sequences from the human hypoxanthine-guanine phosphoribosyl transferase locus. Plasmid pXGH302 utilizes the pTZ18R (Pharmacia P-L Biochemicals, Inc.) backbone, a derivative of plasmid pUC18 (Yanisch-Perron et al., Gene 33: 103–119, 1985) carrying a T7 RNA polymerase promoter and the f1 origin of replication.

Example III

This example illustrates a method of making a hybrid collagen matrix in which transfected cells prepared as described above are precultured with the microspheres prior to formation of the hybrid collagen matrix. Such "precultured" hybrid collagen matrices are referred to as PCHCM.

A. Preculture of cells and microspheres

Trypsinized transfected cells are seeded onto washed collagen microspheres at a ratio of $2 \times 10^6$ cells per ml microspheres (e.g. $10 \times 10^6$ cells onto 5 ml microspheres) by the following protocol:

1. Add cell suspension in a volume of growth medium that is twice the volume of the microspheres to a 125 ml Erlenmeyer flask. The limit is 10 ml of microspheres per flask.

2. Remove 1–2 ml of this suspension and add to 5 ml (packed volume) microspheres premeasured in a 15 ml tube.

3. Transfer cell suspension/microspheres back into the 125 ml Erlenmeyer flask.

4. Place flask into tissue culture incubator and swirl gently for approximately 5 seconds each hour for 4–5 h. Add growth medium to the 50 ml gradation on the flask, and allow cells and microspheres to incubate undisturbed overnight.

After 20–24 h from the time of seeding, determine the number of cells attached to collagen microspheres by the following procedure:

1. Determine the weight of a 5 ml round bottom polystyrene test tube.

2. Remove a small sample of microspheres (0.1–0.2 ml) from the Erlenmeyer flask and add to the pre-weighed test tube.

3. Aspirate medium from microsphere sample and determine the weight of the tube plus sample. Calculate sample weight by subtracting weight of tube from weight of tube plus sample.

4. Add 1 ml of matrix digestion enzyme [collagenase IA (Sigma cat #C9891) at 1–2 mg/ml in PBS with $Ca^{2+}$ and $Mg^{2+}$] to microsphere sample and mix gently by tapping on the side of the tube.

5. Cover the tube with parafilm and place in a 37° C. water bath for 1 h, promoting disintegration of microspheres by pipetting through a Pasteur pipette at minute intervals.

6. After 1 h incubation, further dissociate cells by pipetting vigorously with a 5 ml glass pipette. (Note: If clumps still remain, add to the tube a solution of 10× trypsin-EDTA at a volume 1/10th that of the volume of collagenase solution added, and incubate an additional 10 min.)

7. Perform cell counts using a hemacytometer.

8. Determine density of cells per ml microspheres using the following formula, which assumes that 50% of the wet packed volume of these microspheres is interstitial: Total number of cells/ml microspheres=1000 mg/(mg weight of sample)×(cell number in sample)×0.5.

The cell/microsphere mixture is transferred from the 125 ml Erlenmeyer flask to a 250 ml spinner flask (Bellco Microcarrier Spinner Flasks, 250 ml, with model #1965-60001 impeller shafts), growth medium is added to the 150 ml gradation mark, and the spinner flask is placed on a magnetic stirrer plate (set at 50 rpm) in a tissue culture incubator. The culture is fed with fresh medium the next day and 3 times weekly thereafter by allowing the microspheres to settle on the bottom of the flask, aspirating "spent" medium to the 50 ml mark on the flask, and adding fresh growth medium to the 200 ml mark. The density of cells per ml microspheres may be determined at desired time points as described above.

B. Preparation of Precultured Hybrid Collagen Matrices (PCHCM)

PCHCM are produced by the following protocol:

1. When the desired density of cells per ml microspheres is achieved (as determined by cell counts), remove microspheres containing cells from the spinner flask.
2. Produce matrices following the procedure outlined above for producing HCM, with the following modifications:
   i. Cells are not trypsinized.
   ii. Add cultured microspheres containing cells to 15 ml graduated conical tube(s), to the desired packed volume (volume=no. of matrices×0.5 ml).
   iii. Add empty microspheres to 15 ml graduated conical tube(s) to the desired packed volume (volume=no. of matrices×0.5 ml).
3. Prepare modified 2x DMEM and calf serum mixture as described in Example I above. Add both empty microspheres (50% of total microsphere volume) and microspheres containing cells (50% of total microsphere volume) to the modified 2x DMEM/calf serum mixture (see Table 2 below). The microsphere/DMEM/calf serum mixture is placed on ice and the appropriate volume of collagen solution is added (rat tail Type I collagen; UBI cat #08-115, diluted to concentration of 4.0 mg/ml in 0.02M acetic acid), as specified in Table 2. The contents of the tube are mixed carefully (avoiding creating bubbles or frothing) using a 10 ml glass pipette, until matrix solution appears homogenous.

C. Cells can be recovered and quantified from a hybrid collagen matrix as follows:

1. Enzymatic Digestion of Hybrid Collagen Matrices
   a. Prepare a solution of collagenase IA (1.0 mg/ml for HCM and PCHCM, 2.0 mg/ml for HCM or PCHCM supplemented with ascorbic acid 2-phosphate and/or TGF-β) in PBS.
   b. Dispense the collagenase solution into 15 ml conical centrifuge tubes at a volume of 1 ml for matrices seeded with $1-5 \times 10^6$ cells and 5 ml for matrices seeded with greater than $5 \times 10^6$ cells per matrix. Prepare as many collagenase tubes as there are matrices to be counted.
   c. Remove each matrix from its dish using flat forceps, and carefully blot the excess fluid from the matrix using an absorbent paper towel (if cells will be discarded after counting) or sterile absorbent pad.
   d. Place each matrix in an individual collagenase-containing tube, cap tightly, and secure onto an orbital shaker set at 40 rpm in a tissue culture incubator.
   e. Incubate the matrices for approximately 1 hour or until digestion is complete. To accelerate digestion, break up the matrices by pipetting at 5 min intervals.
2. Cell Counting
   a. Measure the total volume of each digested cell suspension using the gradations on the side of the centrifuge tube.
   b. For measuring cell viability, remove 0.1 ml of cell suspension and add to 0.1 ml of 0.08% trypan blue in a 1.5 ml microcentrifuge tube. Mix by tapping the tube lightly.

TABLE 2

Medium, Microsphere, and Collagen Volumes Used for PCHCM Production

| Dish Size | Number of Matrices | Mod. 2XDMEM | Serum | Microspheres Empty | Microspheres Cultured | Collagen Solution | Total Vol. |
|---|---|---|---|---|---|---|---|
| 60 mm | 1 | 1 ml | 1 ml | 0.5 ml | 0.5 ml | 1 ml | 4 ml |
| 60 mm | 12 | 12 ml | 12 ml | 6 ml | 6 ml | 12 ml | 48 ml |
| 100 mm | 1 | 2.5 ml | 2.5 ml | 1.25 ml | 1.25 ml | 2.5 ml | 10 ml |
| 100 mm | 12 | 30 ml | 30 ml | 15 ml | 15 ml | 30 ml | 120 ml |
| 150 mm | 1 | 7.5 ml | 7.5 ml | 3.75 ml | 3.75 ml | 7.5 ml | 30 ml |
| 150 mm | 12 | 90 ml | 90 ml | 45 ml | 45 ml | 90 ml | 360 ml |

Example IV

A. Hybrid matrices (HCM or PCHCM) are maintained in culture by feeding the matrices on day 1, and then 2 to 3 times weekly using the following protocol:

1. Carefully aspirate the culture medium.
2. Add the required volume of appropriate growth medium, taking into consideration the size of the dish used for each matrix (5–7 ml per 60 mm dish, 10–15 ml per 100 mm dish, 30–40 ml per 150 mm dish). The medium may be supplemented with ascorbic acid 2-phosphate and/or TGF-β (e.g. 10–50 μg/ml ascorbic acid 2-phosphate and/or 1–0 ng/ml TGF-β).

B. The diameter of a hybrid collagen matrix can be determined using the following procedure:

1. Place the petri dish containing the matrix to be measured on top of a metric ruler resting on a dark background.
2. Record diameters (in centimeters) as desired: e.g., daily for the first 2 weeks, every other day after the first 2 weeks, and on days of cell quantitation for the duration of the experiment.

c. Count the viable and dead cells using a hemacytometer. If necessary, further dilute the cell suspension in PBS prior to adding the trypan blue. Calculate the total number of cells, taking into consideration the total volume measured in step 2a.

Example V

This example describes experiments varying the inoculum density of clones of human fibroblasts stably transfected with the plasmid pXGH302 in a hybrid collagen matrix, to determine the cell density that can be supported in HCM. hGH production by each HCM was also monitored.

Hybrid collagen matrices were produced with 3 inoculum densities (ID) of the stably transfected hGH-expressing neonatal foreskin fibroblast clone designated HF165-24. The densities were 5, 10, and $20 \times 10^6$ cells per HCM. For each ID, 9 HCM were produced in 60 mm dishes. The hybrid matrix production medium for each ID consisted of 9 ml of modified 2x DMEM, 9 ml of calf serum, 9 ml of collagen microspheres, and 9 ml of 4 mg/ml soluble rat tail collagen, in 50 ml conical tubes.

HF165-24 harvested from monolayer cultures were pooled to provide enough of each ID for 9 HCM:

$5\times10^6$ cells times 9 HCM=$45\times10^6$ cells total;

$10\times10^6$ cells times 9 HCM=$90\times10^6$ cells total;

$20\times10^6$ cells times 9 HCM=$180\times10^6$ cells total.

Pooled cells for each ID were centrifuged at 1500 rpm for 7 min, supernatant was aspirated, and pellets were resuspended in 9 ml modified 2x DMEM and 9 ml calf serum and transferred to 50 ml tubes. Nine ml of collagen microspheres pre-measured in 15 ml graduated tubes were added to the cells/2x DMEM/calf serum mixture and mixed by gentle pipetting with a 10 ml pipette. This mixture was then placed on ice, and 9 ml of ice cold rat tail type I collagen solution (4 mg/ml) was added and mixed with a 10 ml pipette to produce a homogenous solution. Four ml of this mixture was added to each of nine 60 mm petri dishes for each density. The petri dishes were set in a tissue culture incubator and left undisturbed for 24 h. Medium was carefully aspirated from each dish after the 24 h incubation, and HCM were re-fed with Growth Medium (DMEM, 10% calf serum, and 1% Pen/Strep), using 5 ml per dish. To provide a greater volume of Growth Medium per matrix, HCMs were transferred on day 3 from 60 mm petri dishes to 100 mm petri dishes using flat forceps, and 10 ml of Growth Medium was added per dish. On day 6, medium was aspirated from each HCM, matrices were rinsed with 5 ml of Hank's Balanced Salt Solution (HBSS) and aspirated, and 10 ml of Growth Medium was added to each dish. The time of Growth Medium addition to HCM was noted in order to take a 24 h medium sample the following day (day 7). This rinse and feeding procedure was repeated on days 13 and 20 to provide day 14 and day 21 medium samples. The medium samples were assayed for hGH as indicated below. The HCM were also refed on days and 17 without the rinse step.

Digestion of 3 HCM per ID for cell counts occurred on days 7, 14, and 21 after medium samples were taken, as described in Example IV. Production of hGH by HCM at the indicated time points was measured by radioimmunoassay (Nichols Institute) of the 24 h medium samples, as described in Example XII below. Table 3 summarizes the cell numbers for triplicate HCM of each ID, and hGH production by HCM at each ID on days 7 (n=9), 14 (n=6), and 21 (n=3). Values are presented as mean +/−standard deviation. As indicated, the equilibrium density determined at days 14 and 21 for HCM prepared as described above is approximately 7–$10^6$ cells per matrix. Per cell hGH production for fully formed matrices at day 21 is similar among the 3 ID levels tested.

TABLE 3

Optimization of the Inoculum Density of HF165- 24 Embedded in Hybrid Matrices for Cell Density and hGH Production.

| HCM ID | Cell # Day 7 | μg hGH/ 24 h/matrix | μg hGH/24 h/ $10^6$ cells |
|---|---|---|---|
| $5\times10^6$ | 5,331,000 ± 279,347 | 683 ± 138 | 130 ± 20 |
| $10\times10^6$ | 9,853,833 ± 858,634 | 716 ± 137 | 73 ± 6 |
| $20\times10^6$ | 13,226,000 ± 1,234,410 | 689 ± 130 | 50 ± 6 |

| HCM ID | Cell # Day 14 | μg hGH/ 24 h/matrix | μg hGH/24 h/ $10^6$ cells |
|---|---|---|---|
| $5\times10^6$ | 6,534,000 ± 344,525 | 853 ± 232 | 133 ± 23 |
| $10\times10^6$ | 9,631,000 ± 875,820 | 1037 ± 277 | 108 ± 12 |
| $20\times10^6$ | 10,360,000 ± 706,541 | 840 ± 280 | 81 ± 16 |

| HCM ID | Cell # Day 21 | μg hGH/ 24 h/matrix | μg hGH/24 h/ $10^6$ cells |
|---|---|---|---|
| $5\times10^6$ | 6,916,167 ± 608,352 | 730 ± 129 | 105 ± 10 |
| $10\times10^6$ | 9,884,833 ± 1,475,327 | 1004 ± 279 | 101 ± 20 |
| $20\times10^6$ | 10,207,750 ± 2,833,250 | 872 ± 333 | 83 ± 10 |

Example VI

"Standard" collagen matrices (CM) do not include collagen microspheres. In order to compare CM with HCM, CM were prepared by replacing the volume occupied by microspheres in HCM with additional soluble collagen, to give a ratio of 1 part 2x DMEM, 1 part calf serum, and 2 parts soluble collagen per CM. A direct comparison of CM with HCM was assessed as follows.

The clone of human fibroblasts stably transfected with the plasmid pXGH302, designated HF165-24, was used. Nine matrices of each type, at each of two ID ($1\times10^6$ and $5\times10^6$ cells per matrix), were produced. For both CM and HCM, $9\times10^6$ cells (for $1\times10^6$ ID) and $45\times10^6$ cells (for $5\times10^6$ ID) were resuspended in 9 ml of 2x DMEM+9 ml of calf serum in 50 ml tubes. For CM, a total of 18 ml of rat tail type I collagen solution (4 mg/ml) was added to each ID set, and matrices were formed as described above in Example I. For HCM, 9 ml collagen microspheres and 9 ml of rat tail type I collagen solution (4 mg/ml) were added to each ID set, and HCM were formed according to Example I. Matrices were kept in the original 60 mm dish and fed with a volume of 5 ml Growth Medium. Cell numbers per matrix, as well as hGH production per matrix, were determined on days 7, 14, and 30 as described for Example V. The maximum cell densities (measured on day 14) and hGH production achieved by the 2 types of matrices at the 2 densities are summarized in Table 4. As indicated in the table, the hybrid type of matrix allowed for a higher density of cells and a substantially greater production of hGH per matrix, compared with the standard collagen matrix without microspheres.

TABLE 4

Comparison of "Standard" Collagen Matrices (CM) and Hybrid Collagen Matrices (HCM) for Maximum Cell Density and hGH Production by Embedded HF165-24 Cells

| Matrix Type | ID | Maximum cell Density | Maximum hGH Production Per matrix |
|---|---|---|---|
| CM | $1\times10^6$ | $2.1\times10^6$ | 290 μg |
| CM | $5\times10^6$ | $3.3\times10^6$ | 299 μg |
| HCM | $1\times10^6$ | $6.2\times10^6$ | 983 μg |
| HCM | $5\times10^6$ | $10.3\times10^6$ | 1221 μg |

Example VII

This example describes the production and analysis of precultured hybrid collagen matrices (PCHCM). Cells of the clone of human fibroblasts stably transfected with the plasmid pXGH302 (HF165-24) were seeded onto collagen microspheres at a ratio of $2 \times 10^6$ cells per ml of microspheres, in the following manner: A suspension of $48 \times 10^6$ cells in 40 ml Growth Medium was obtained from harvested monolayer cultures. 5 ml of this suspension was added to each of four 15 ml graduated tubes containing 6 ml of packed collagen microspheres, and each cell/microsphere mixture was transferred to a 125 ml Erlenmeyer flask. An additional 5 ml of cell suspension was added to the cell/microsphere mixture in the 125 ml Erlenmeyer flask to give a final suspension of $12 \times 10^6$ cells with 6 ml microspheres and 10 ml Growth Medium per flask (4 flasks total). The flasks were placed in a tissue culture incubator and swirled gently for approximately 5 seconds each hour for 4 h. After the fourth hour, Growth Medium was added to each flask to the 50 ml mark, and flasks were left undisturbed for 24 h. At 24 h, the microspheres were transferred from each Erlenmeyer flask into a 250 ml spinner flask, Growth Medium was added to the 150 ml mark of each spinner flask, and flasks were placed on a magnetic stirrer plate set at 50 rpm in a tissue culture incubator. The following day, Growth Medium was added up to the 200 ml mark of each spinner flask, and flasks were refed 3 times weekly by aspirating medium to the 50 ml mark and adding fresh medium up to 200 ml.

On day 15 of the spinner flask culture, the density of cells per ml microspheres was determined. A small sample of microspheres (~0.1×0.2 ml) was removed from each flask and placed in pre-weighed 5 ml polystyrene tubes. Excess medium was removed from each tube by aspiration, and the tube containing the microsphere sample was weighed. One ml of a 2 mg/ml collagenase type IA solution in PBS was added to each tube, and the tubes were covered with parafilm, and placed in a 37° C. waterbath. At 15 minute intervals, the tubes containing microspheres were tapped lightly to disperse clumps. After 1 h, cells were further dissociated by vigorous pipetting with a 5 ml glass pipette. To further dissociate clumps, a solution of 10x trypsin:EDTA was added to give a final trypsin concentration of 1x in the collagenase solution, and the tubes were incubated for an additional 10 minutes. The dissociated cell suspensions were diluted 1:2 with PBS and added to hemacytometer chambers for cell counting. The density of cells per ml microspheres was calculated using the following formula:

Total # of cells/ml microspheres=1000 mg/(mg weight of sample)×(cell# in sample)×0.5.

This formula assumes that 1) wet collagen has a specific gravity of 1.0, and therefore the gram weight of collagen in the microsphere sample equals the collagen volume in milliliters, and 2) half of the wet packed volume of microspheres is occupied by interstitial volume. The average number of cells per ml microspheres (n=4) for this experiment was $19.2 \times 10^6$. Microspheres were removed from each flask and pooled in a 15 ml graduated tube. The entire volume of 6 ml microspheres containing $19.2 \times 10^6$ cells per ml microspheres was used to produce hybrid collagen matrices.

In a 100 ml sterile bottle, 12 ml of modified 2x DMEM, 12 ml of calf serum, 6 ml of empty collagen microspheres, and the 6 ml of precultured microspheres were carefully mixed using a 10 ml glass pipette. This mixture was placed on ice, and 12 ml of ice-cold rat tail Type I collagen was added and mixed carefully using a 10 ml glass pipette. 4 ml of this mixture was added to each of twelve 60 mm petri dishes, and the dishes were placed at 37° C. and left undisturbed for 24 h.

The final number of cells per matrix was $9.6 \times 10^6$, since each matrix was composed of 0.5 ml of microspheres containing $19.2 \times 10^6$ cells per ml. These precultured hybrid collagen matrices (PCHCM) were refed after 24 h by aspirating the medium and adding 5 ml of Growth Medium. The PCHCM were refed on days 4, 7, 11, 14, 18, and 20 with 6 ml of Growth Medium. On days 7, 14, and 20, the PCHCM were also rinsed with 4 ml of HBSS prior to addition of medium, and the time of medium addition was noted. On days 8, 15, and 21, a 24 h medium sample was taken for assay of hGH production, and PCHCM were digested to obtain cell counts as follows: A solution of 2 mg/ml collagenase type IA in PBS was added at a volume of 6 ml per 15 ml tube. PCHCM were lifted from dishes with flat forceps and blotted on an absorbent paper towel prior to transfer into a collagenase solution. Tubes containing PCHCM and collagenase solution were secured onto an orbital shaker in a tissue culture incubator, the speed was set to 40 rpm, and PCHCM were allowed to digest for 2 h. After the 2 h incubation, PCHCM were dissociated into single cells by vigorous pipetting with a 5 ml glass pipette. Further dissociation was deemed necessary due to the presence of clumps, and a solution of 10x trypsin:EDTA (0.5% trypsin, 5.3 mM EDTA) was added to give a final trypsin concentration of 1X in the collagenase. The tubes were then incubated for an additional 10 min. Volumes in each tube were noted, and cell suspensions were diluted 2-fold in PBS and placed in a hemacytometer chamber to obtain cell counts. Production of hGH by PCHCM at the indicated time points was measured by radioimmunoassay of the 24 h medium samples, as described in Example VIII. Table 5 summarizes the cell numbers for triplicate PCHCM at each time point, and hGH production by PCHCM on days 8 (n=12), 15 (n=9), and 21 (n=6). Values are presented as mean±standard deviation. As Table 5 shows, these PCHCM support a higher density of cells than the HCM described in Examples V and VI (Tables 3 and 4). The rate of hGH production per matrix and per cell was similar throughout the study period.

TABLE 5

HF165-24 Precultured on Collagen Microspheres and Embedded in Collagen to Form PCHCM: Cell Number and hGH production Over Time in Culture.

| Day | Cell Number | μg hGH/24 h/matrix | μg hGH/24 h/$10^6$ cells |
|---|---|---|---|
| 8 | 13,732,000 ± 1,786,565 | 1264 ± 155 | 94 ± 10 |
| 15 | 12,573,000 ± 1,547,133 | 1317 ± 166 | 97 ± 14 |
| 21 | 13,706,000 ± 497,073 | 1254 ± 135 | 85 ± 10 |

Example VIII hGH expression was monitored by quantitative hGH measurement with a sandwich radioimmunometric assay (Allegro hGH Assay, Nichols Institute, Cat. No. 40-2205), using conditions recommended by the manufacturer.

In order to determine the rate of hGH production, culture medium was changed 24 hours prior to harvesting the cells for passaging. At the time of passage an aliquot of the culture medium was removed for hGH assay, and the cells were then harvested, counted, and reseeded. hGH levels are calculated after counting the harvested cells, and are expressed as µg hGH/24 hr/$10^6$ cells.

Example IX

This example describes in vivo implantation of hybrid collagen matrices (HCM) prepared as described in Example I, as well as standard collagen matrices (CM) prepared as described in Example VI.

For subcutaneous implantation of matrices, mice [*M. musculus* strains N:NIH(S)-nu/nu (nude; Taconic Farms, Germantown, N.Y.) were given an intraperitoneal injection of avertin (solution of 2% w/v 2,2,2-tribromoethanol and 2% v/v 2-methyl, 2-butanol) at a dose of 0.0175 ml/g body weight. Anesthetized mice were placed in lateral recumbency, and the skin prepped with alcohol and Betadine. A 0.5 cm to 1 cm transverse incision was made on the animal's left flank. The subcutaneous space was enlarged by sharp dissection to an area slightly larger than the size of the matrix to be implanted. The matrix was placed horizontally in the subcutaneous space and spread evenly with the use of Millipore forceps. The incision was closed, using stainless steel surgical staples.

Blood was collected by retroorbital bleed after placing the mouse in a large beaker containing methoxyflurane (Pittman-Moore) until light anesthesia was achieved. Serum hGH levels were determined using the commercially available sandwich radioimmunometric assay described above. The assay was performed as described as recommended, except that control serum from untreated mice was used to obtain corrected cpm for generating the standard curve.

CM and HCM were prepared for implantation into nude mice as described in Examples I and VI, using hGH-expressing HF165-24 cells. In the first experiment (Experiment 1, Tables 6 and 7), 13 matrices of each type were prepared. HCM were produced with an inoculum density (ID) of $5 \times 10^6$ HF165-24 cells per matrix, and standard collagen matrices (CM) were produced with an ID of $2 \times 10^6$ HF165-24 per matrix. Fewer cells were used to inoculate the CM since these matrices do not support as high a cell density as HCM (see Examples V and VI). In subsequent experiments (Experiments 2 and 3, Tables 6 and 7) only HCM matrices were tested (13 in each of Experiments 2 and 3). Matrices were kept in the original 60 mm dishes and fed with 5 ml of growth medium. After 13 days in culture, all of the dishes were fed with fresh growth medium; 24 h later triplicate matrices of each set were digested for cell counts, and medium samples from all 13 matrices in each set were assayed for hGH.

For Experiment 1, at the time of implantation the average number of cells in the CM was $2.4 \times 10^6$ cells/matrix, while the average number of cells in the HCM was $7.4 \times 10^6$ cells/matrix (Table 6). The cell number per matrix was similar to the latter for the HCM prepared in Experiments 2 and 3 ($8.9 \times 10^6$ and $9.2 \times 10^6$ cells per HCM matrix, respectively). Table 6 summarizes the cell number (n=3), in vitro hGH production per matrix (n=13), and specific production rate (µg/$10^6$cells/24 h; n=3) for each set of in vitro experiments. Values are presented as mean±standard deviation. As shown in Table 6, HCM supported a higher density of cells and produced a higher level of hGH on the day of implantation than did the CM.

TABLE 6

HF165-24 Cell Density and In Vitro hGH Production per Matrix for Collagen Matrices and Hybrid Collagen Matrices on Day of Implantation

| Experiment # | Cell # on Day of Implantation | µg hGH/ 24 h/ matrix | µg hGH/ 24 h/ $10^6$ cells |
|---|---|---|---|
| 1/CM | $2.4 \pm 0.1 \times 10^6$ | 241 ± 33 | 98 ± 8 |
| 1/HCM | $7.4 \pm 1.6 \times 10^6$ | 983 ± 239 | 109 ± 16 |
| 2/HCM | $8.9 \pm 1.5 \times 10^6$ | 1399 ± 177 | 170 ± 27 |
| 3/HCM | $9.2 \pm 0.9 \times 10^6$ | 1279 ± 115 | 137 ± 19 |

Figure 3:
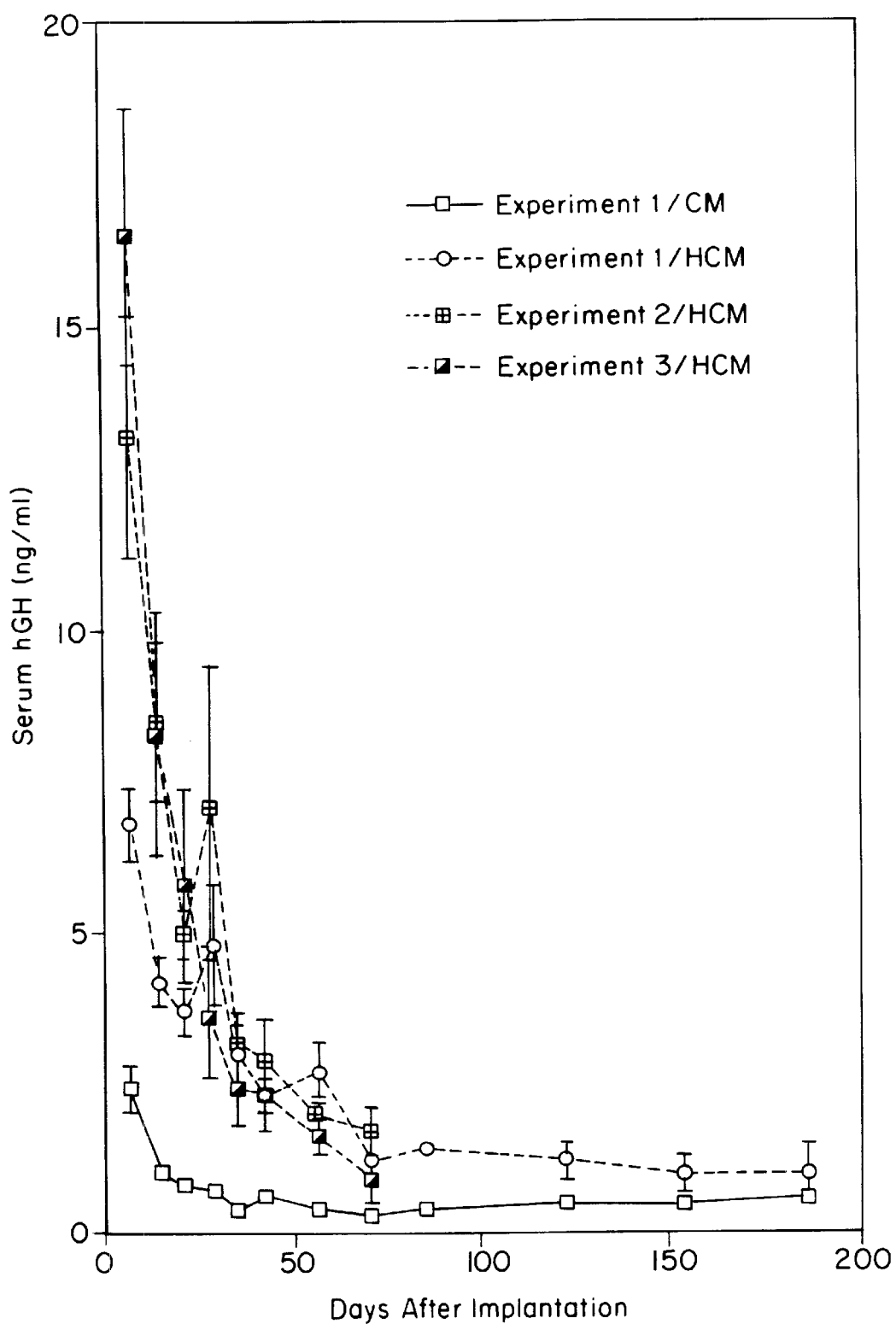
FIG. 3 is a graph showing the in vivo hGH levels in nude mice implanted with either a collagen matrix or a hybrid collagen matrix containing HF165-24 cells, human skin fibroblasts stably transfected with pXGH302 and expressing hGH.

Eight matrices of each type were implanted into nude mice in Experiment 1, while five HCM were implanted into nude mice in each of Experiments 2 and 3. Serum hGH levels were measured at regular intervals after implantation. The results are shown in Table 7 and FIG. 3. In Experiment 1, HCM-implanted animals maintained substantially higher serum hGH levels than did CM-implanted animals for 186 days post-implantation. Animals implanted with HCM in Experiments 2 and 3 showed similarly high serum hGH levels.

TABLE 7

In Vivo Delivery of hGH by Implanted Collagen Hybrid Matrices Containing Transfected Human Skin Fibroblasts serum hGH values (ng/ml ± standard error)

| Days After Implantation | Experiment 1 CM n = 8 | Experiment 1 HCM n = 8 | Experiment 2 HCM n = 5 | Experiment 3 HCM n = 5 |
|---|---|---|---|---|
| 7 | 2.4 ± 0.4 | 6.8 ± 0.6 | 13.2 ± 2.0 | 16.5 ± 2.1 |
| 14 | | | 8.5 ± 1.3 | 8.3 ± 2.0 |
| 15 | 1.0 ± 0.1 | 4.2 ± 0.4 | | |
| 21 | 0.8 ± 0.1 | 3.7 ± 0.4 | 5.0 ± 0.4 | 5.8 ± 1.6 |
| 28 | | | 7.1 ± 2.3 | 3.6 ± 1.0 |
| 29 | 0.7 ± 0.1 | 4.8 ± 1.0 | | |
| 35 | 0.4 ± 0.1 | 3.0 ± 0.7 | 3.2 ± 0.3 | 2.4 ± 0.6 |
| 42 | 0.6 ± 0.1 | 2.3 ± 0.3 | 2.9 ± 0.7 | 2.3 ± 0.6 |
| 55 | | | 2.0 ± 0.3 | |
| 56 | 0.4 ± 0.1 | 2.7 ± 0.5 | | 1.6 ± 0.3 |
| 70 | 0.3 ± 0.0 | 1.2 ± 0.2 | 1.7 ± 0.4 | 0.9 ± 0.4 |
| 85 | 0.4 ± 0.1 | 1.4 ± 0.2 | | |
| 123 | 0.5 ± 0.1 | 1.2 ± 0.3 | | |
| 154 | 0.5 ± 0.1 | 1.0 ± 0.3 | | |
| 186 | 0.6 ± 0.1 | 1.0 ± 0.5 | | |

Example X

The hybrid matrices of the invention would be prepared for implantation in humans as follows:

The desired cells, typically stably transfected autologous cells derived from the patient, are harvested from tissue culture dishes and processed for the production of HCM or PCHCM by any of the methods described in Examples I–IV. The dosage for a given patient (i.e. the physiologically effective quantity of therapeutic product produced by the matrix) can be varied by using a larger or smaller matrix, implanting a different number of matrices into the patient, and/or using cells which express a different level of the product per cell when constructing the matrix. The quantity of the therapeutic product produced in the patient may also be varied by exposing the cells in the matrix to a pharmacologic or physiologic signal which alters expression of the therapeutic gene. For example, if the therapeutic gene is under the control of a glucocorticoid-responsive promoter, then in vivo exposure of the cells to a drug such as dexamethasone (by administering the drug to the patient in a manner that ensures the drug reaches the implant) will alter expression of the therapeutic gene.

Typically, a plurality of small matrices (approximately 1–2 cm) in diameter, produced in 60 mm petri dishes and containing on the order of $10 \times 10^6$ cells per matrix, would be implanted. Thus, approximately 100 million cells could be implanted using 10 small matrices. The use of matrices with significantly higher cell densities (as produced by incorporating, for example, ascorbic acid 2-phosphate) would result in a smaller number of matrices needed for a given patient. Alternatively, a larger petri dish (>150 mm diameter) may be used as a mold to produce larger matrices which could be either implanted directly or cut into smaller pieces which are implanted.

Prior to implantation, the matrices may be stored or shipped in growth medium or any other solution which allows the cells to remain viable. Alternatively, the matrices may be cryopreserved by freezing in an appropriate freezing medium, which can be washed away prior to implantation.

Matrices may be implanted in a variety of sites, including, but not limited to, subcutaneous, intraperitoneal, intrasplenic, intraomental, inguinal, intrathecal, intraventricular, and intramuscular sites, as well as within lymph nodes or within adipose tissue. A surgical incision at the appropriate site is made, the matrix inserted, and the incision closed.

Example XI

There are a number of static and perfusion large scale in vitro culture systems that can be adapted for use in protein manufacture using cells maintained in hybrid matrices of the invention. The choices offer varying levels of facility in the necessary steps of feeding and medium harvest prior to purification of target proteins. Several are described below.

1. After formation and maturation of hybrid collagen matrices (HCM) in conventional petri plates (e.g. after 10–25 days incubation), a number of these HCM can be aseptically transferred to a sterile Microcarrier Spinner Flask (250–100 ml capacity). These HCM are produced and maintained under conditions which maximize the viable cell density within each matrix. Typically this requires between 5 and 20 ml medium for every one ml of matrix volume. The protein production medium is formulated to comprise a minimum of undefined components (e.g., serum), and may include added factors intended to maximize the output of protein production per cell. The spinner flasks are placed into a $37°\pm1°$ C., $5\%\pm1\%$ $CO_2$ humidified incubator on a magnetic stir platform set for 30–70 rpm. After 1–3 days, the flask is transferred to a class 100 biological safety cabinet, and the production medium containing the expressed protein is aseptically drawn off without disturbing the settled matrices. An equivalent volume of fresh protein production medium is added to the flask, and the flask is returned to the stir platform within the incubator.

2. The matrices described in (1) above may be aseptically transferred into a 1–5 L bioreactor (e.g., Brunswick) with a controllable stirring impeller shaft. Production medium level is set by the control system of the bioreactor. Medium harvesting and replenishment is controlled within a sterile closed loop system to minimize contamination.

3. For high volume HCM production, the matrices are formed from the constituent components and allowed to gel within a tissue culture roller bottle. The bottles are incubated in a static upright position until contraction of the matrix results in a free-floating structure (3–5 days). Growth medium is then replenished, and the bottles are gassed with 5% $CO_2$ and placed into a roller apparatus within a 37° C. incubator. Growth medium is replenished every 2–3 days until HCM are mature (10–25 days total incubation), at which time the HCM are exposed to protein production medium. After 1–3 days, the bottles are transferred to a class 100 biological safety cabinet and the production medium containing the expressed protein is aseptically drawn off without disturbing the matrices. An equivalent volume of fresh protein production medium is added to the bottle, which is returned to the roller apparatus.

4. The constituents of the HCM can be aseptically introduced into sterile gas-permeable Teflon® bags through a sealable port. The components are allowed to gel within the bag and take on the shape and conformation therein. Bags are incubated in $37°\pm1°$ C., $5\%\pm1\%$ $CO_2$ humidified incubators. As the HCM contract and reduce in volume, the growth medium volume is adjusted to compensate. Medium harvesting and replenishment is accomplished through sterile-connect tube systems built into the bags. The use of ported incubators and extended tubing would allow for the design of a cyclic harvest/feed pumping system that could eliminate the need for removing the bags from incubators during a production run.

5. The constituents of the HCM can be aseptically introduced into custom-designed thermoformed trays with a high volume capacity. The simplest conformation would be an open lidded rectangular tray with gas exchange capabilities designed for use in a $CO_2$ tissue culture incubator. Another design would include a closed loop system with ported access to the medium reservoir for controlled feeding and medium harvest, akin to a bioreactor chamber.

Other Embodiments

The hybrid matrices of the invention are appropriate or delivery of a wide range of cellular products, including not only hGH, but also Factor VIII, Factor IX, erythropoietin (EPO), albumin, hemoglobin, alpha-1 antitrypsin, calcitonin, glucocerebrosidase, low density lipoprotein (LDL) receptor, IL-2 receptor, globin, immunoglobulin, catalytic antibodies, the interleukins, insulin, insulin-like growth factor 1 (IGF-1), parathyroid hormone (PTH), leptin, the interferons, the nerve growth factors, basic fibroblast growth factor (bFGF), acidic FGF (aFGF), epidermal growth factor (EGF), endothelial cell growth factor, platelet derived growth factor (PDGF), transforming growth factors, endothelial cell stimulating angiogenesis factor (ESAF), angiogenin, tissue plasminogen activator (t-PA), granulocyte colony stimulating factor (G-CSF), and granulocyte-macrophage colony stimulating factor (GM-CSF). For example, the cells embedded in the matrix can be pancreatic beta cells which naturally secrete insulin in response to a rise in blood glucose, and which therefore can supplement an inadequate insulin response in a diabetic or pre-diabetic patient. Alternatively, they can be any type of cell genetically engineered to express and secrete high levels of a needed polypeptide, such as a clotting factor, within the patient. Such a construct may be under the control of a constitutively activated promoter, or of an appropriately physiologically or pharmacologically regulated promoter.

The collagen gel portion of the matrix can consist entirely of insoluble collagen fibrils, or can contain other components in addition to collagen: e.g., agarose; alginate; a glycosaminoglycan such as hyaluronic acid, heparin sulfate, dermatan sulfate, or chondroitin sulfate; a sulfated proteoglycan; fibronectin; laminin; elastin; fibrin; or tenascin. Such components (particularly those which are found in the extracellular matrix of animal tissues) contribute to the structural stability of the hybrid matrices of the invention, and/or provide additional attachment capacity for the cells in the matrices and the host tissue at the site of implantation. They would be incorporated into the matrices by mixing with the collagen solution prior to gelling.

Other potential additives include cytokines and/or growth factors which are useful for optimizing maintenance of the cells or promoting beneficial interaction with host tissue (e.g., vascularization), including bFGF, aFGF, endothelial cell growth factor, PDGF, endothelial cell stimulating angiogenesis factor (ESAF), leukotriene $C_4$, prostaglandins (e.g., $PGE_1$, $PGE_2$), IGF-1, GCSF, angiogenin, TGF-$\alpha$, TGF-$\beta$, ascorbic acid, EGF, and oncostatin M. These additives can be incorporated into the matrix by mixing them with the collagen solution prior to gelling, by introducing them into the interstices of the microspheres, or by including them in the medium which bathes the matrices. Alternatively, the cells may be genetically engineered to express the desired product. For example, the cells of the matrix may be cotransfected with a DNA encoding an angiogenesis factor and a DNA encoding a second, therapeutic protein, or with a single vector encoding both types of proteins linked to suitable expression control sequences.

The collagen used in the gel may be any suitable type (e.g., type I-XI), or a mixture of any two or more. Fibers may be placed in the mold prior to gelling of the collagen, so that they become an integral part of the matrix and contribute to the sturdiness and handling convenience of the matrix. Typically, the fibers would be made principally of collagen (e.g., cat gut) or a non-collagenous material such as nylon, dacron, polytetrafluoroethylene (Gore-Tex® or Teflon® ), polyglycolic acid, polylactic/polyglycolic acid mixture (Vicryl®), polystyrene, polyvinylchloride co-polymer, cellulose (e.g., cotton or linen), polyester, rayon, or silk. The fibers may be woven into a mesh or cloth, or used as individual threads.

Instead of the type I collagen microspheres described in the above examples, one could utilize microspheres consisting primarily of another type of collagen, polystyrene, dextran (e.g., Cytodex®, Pharmacia), polyacrylamide, cellulose, calcium alginate, latex, polysulfone, glass (coated with a substance such as collagen which promotes cellular adherence), or combinations of collagen with any of the above. Such microspheres are available commercially or can be made by standard methods, then sterilized for use in the hybrid matrices of the invention.

Other embodiments are within the following claims.

What is claimed is:

1. An extracorporeal apparatus comprising:
   a composition comprising a body of matrix material comprising insoluble collagen fibrils, there being embedded within the body of matrix material (a) a plurality of cultured vertebrate cells and (b) a plurality of microspheres; and
   a means for shunting blood from an animal to the composition and then back into a blood vessel of the animal.

2. The apparatus of claim 1, wherein the cultured vertebrate cells express and secrete a medically useful polypeptide.

3. The apparatus of claim 2, wherein the cultured vertebrate cells are genetically engineered to express the medically useful peptide.

4. The apparatus of claim 1, wherein the cultured vertebrate cells are selected from the group consisting of adipocytes, astrocytes, cardiac muscle cells, chondrocytes, endothelial cells, epithelial cells, fibroblasts, gangliocytes, glandular cells, glial cells, hematopoietic cells, hepatocytes, keratinocytes, myoblasts, neural cells, osteoblasts, pancreatic beta cells, renal cells, smooth muscle cells, striated muscle cells, and precursors of any of the above.

5. The apparatus of claim 1, wherein the cultured vertebrate cells are human cells.

6. The apparatus of claim 3, wherein the cultured vertebrate cells are transfected cells containing exogenous DNA encoding the polypeptide.

7. The apparatus of claim 3, wherein the cultured vertebrate cells are transfected cells containing exogenous DNA which includes a regulatory sequence that activates expression of a gene encoding the polypeptide, said gene being endogenous to said vertebrate cells both prior to and after they are transfected.

8. The apparatus of claim 2, wherein the polypeptide is selected from the group consisting of enzymes, hormones, cytokines, colony stimulating factors, vaccine antigens, antibodies, clotting factors, regulatory proteins, transcription factors, receptors, and structural proteins.

9. The apparatus of claim 2, wherein the polypeptide is an angiogenesis factor.

10. The apparatus of claim 2, wherein the polypeptide is selected from the group consisting of human growth hormone, Factor VIII, Factor IX, erythropoietin, and insulin.

11. The apparatus of claim 3, wherein the polypeptide is selected from the group consisting of human growth hormone, Factor VIII, Factor IX, erythropoietin, and insulin.

12. The apparatus of claim 2, wherein the cultured vertebrate cells secrete a polypeptide selected from the group consisting of alpha-1 antitrypsin, calcitonin, glucocerebrosidase, low density lipoprotein (LDL) receptor, IL-2 receptor, globin, immunoglobulin, catalytic antibodies, the interleukins, insulin-like growth factor 1 (IGF-1), parathyroid hormone (PTH), leptin, the interferons, the nerve growth factors, basic fibroblast growth factor (bFGF), acidic FGF (aFGF), epidermal growth factor (EGF), endothelial cell growth factor, platelet derived growth factor (PDGF), transforming growth factors, endothelial cell stimulating angiogenesis factor (ESAF), angiogenin, tissue plasminogen activator (t-PA), granulocyte colony stimulating factor (G-CSF), and granulocyte-macrophage colony stimulating factor (GM-CSF).

13. The apparatus of claim 1, wherein the microspheres are beads of type I collagen.

14. The apparatus of claim 1, wherein the matrix material additionally comprises a substance selected from the group consisting of a second type of collagen, agarose, alginate, fibronectin, laminin, hyaluronic acid, heparan sulfate, dermatan sulfate, sulfated proteoglycans, fibrin, elastin, and tenascin.

15. The apparatus of claim 1, wherein noncollagen fibers are dispersed within the body of matrix material.

16. The apparatus of claim 15, wherein the noncollagen fibers comprise a material selected from the group consisting of nylon, dacron, polytetrafluoroethylene, polyglycolic acid, polylactic/polyglycolic acid mixture, polystyrene, polyvinylchloride copolymer, cat gut, cotton, linen, polyester and silk.

17. The apparatus of claim 1, wherein each of the plurality of microspheres consists primarily of one or more substances selected from the list consisting of collagen, polystyrene, dextran, polyacrylamide, cellulose, calcium alginate, latex, polysulfone, and glass.

18. The apparatus of claim 1, wherein the microspheres have a diameter between approximately 0.1 and approximately 2 mm.

19. The apparatus of claim 1, wherein the collagen in the matrix material is type I collagen.

20. A method of administering a polypeptide to a patient in need thereof, comprising
   providing the extracorporeal apparatus of claim 2; and
   shunting a portion of the patient's blood through the apparatus and back into the patient's bloodstream, so that the polypeptide secreted by the cells mixes with the blood.

* * * * *

UNITED STATES PATENT AND TRADEMARK OFFICE
CERTIFICATE OF CORRECTION

PATENT NO. : 6,582,391 B2
DATED : June 24, 2003
INVENTOR(S) : Rochelle Mineau-Hanschke It is certified that error appears in the above-identified patent and that said Letters Patent is hereby corrected as shown below:

Title page,
Item [56], References Cited, OTHER PUBLICATIONS,
"Demetriou et aL." should be -- Demetriou et al. --.
"Halberstadt et al." reference, delete the "Ω" at the end of the second line of the reference.
"Kleinman ofet at.," should be -- Kleinman et al., --.
"Moullier et Al.," should be -- Moullier et al., --.
"Nakajima et al." reference, "Adipose tissue extracellular matrix: newly organized by adipocytes during differentiation Differentiation 63(4):" should be -- Adipose tissue extracellular matrix: newly organized by adipocytes during differentiation, Differentiation 63(4): --.
"Nakagawa et at.," should be -- Nakagawa et al., --.
"Palmer et at.," should be -- Palmer et al., --.
Second "Palmer et al." reference delete one of the "," after the title and before the "Blood 73:".
"Shahar et at.," should be -- Shahar et al., --.
"Turley et at.," should be -- Turley et al., --.
"Turley et al." reference, "The Retention and Uttrastructural Appearances of Various Extracetlular Matrix Molecules Incorporated into Three-Dimensional Hydrated Collagen Lattices," should be -- The Retention and Ultrastructural Appearances of Various Extracellular Matrix Molecules Incorporated into Three-Dimensional Hydrated Collagen Lattices, --.
"Varani et at.," should be -- Varani et al., --.
"Weinberg and Bell" reference, "Regulation of Proliferation of Bovine Aortic Endothelial Cells, Smooth Muscle Cells, a Adventitial Fibroblasts in Collagen Lattices," should be -- Regulation of Proliferation of Bovine Aortic Endothelial Cells, Smooth Muscle Cells, an Adventitial Fibroblasts in Collagen Lattices, --.

UNITED STATES PATENT AND TRADEMARK OFFICE
CERTIFICATE OF CORRECTION

PATENT NO.   : 6,582,391 B2
DATED        : June 24, 2003
INVENTOR(S)  : Rochelle Mineau-Hanschke It is certified that error appears in the above-identified patent and that said Letters Patent is hereby corrected as shown below:

Title page (cont'd),
"Dang et al." reference, "Gene Therapy and Translational Caner Research" should be -- Gene Therapy and Translational Cancer Research --.

Signed and Sealed this

Tenth Day of February, 2004

JON W. DUDAS
*Acting Director of the United States Patent and Trademark Office*